Nov. 8, 1955 H. C. SWIM Plant Pat. 1,435
ROSE PLANT
Filed Oct. 25, 1954
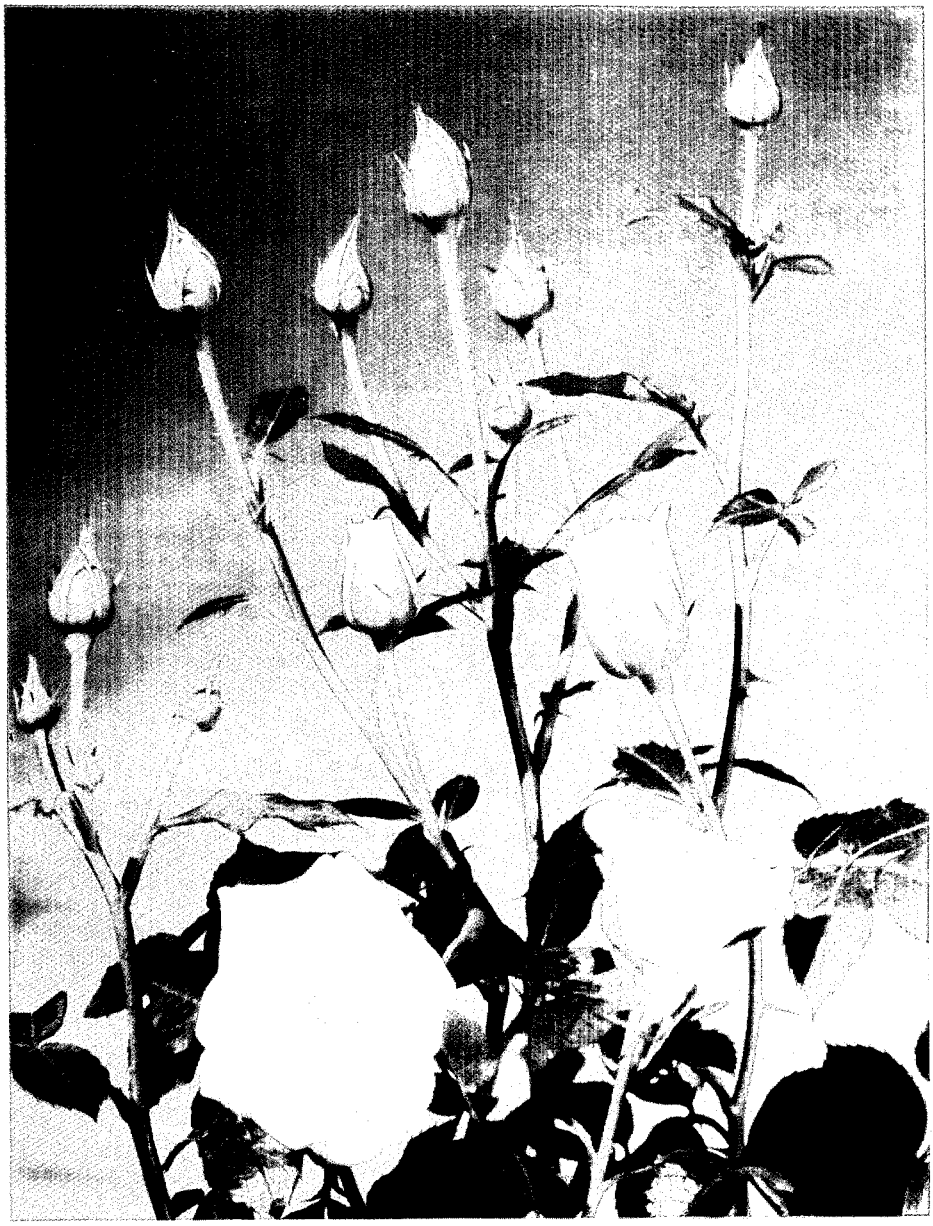
Inventor.
H. C. Swim
By: Robert Robb
Attorneys.

United States Patent Office

Plant Pat. 1,435
Patented Nov. 8, 1955

1,435

ROSE PLANT

Herbert C. Swim, Ontario, Calif., assignor to Armstrong Nurseries, Inc., Ontario, Calif., a corporation of California Application October 25, 1954, Serial No. 464,663

1 Claim. (Cl. 47—61)

The present invention relates to a new and distinct variety of rose plant of the hybrid polyantha class, which was originated by me by crossing the variety "Goldilocks" (Plant Patent No. 672) with the variety "Pinocchio" (Plant Patent No. 484).

The primary objective in making this cross was to combine the most desirable characteristics of the two parent varieties, with the resulting creation of a new variety having a unique and more desirable combination of characteristics. This objective was fully achieved, with the attainment of a still further improvement in my new variety, making the same suitable for greenhouse production of cut flowers as well as for garden use. In particular, my new variety is characterized as to novelty by the following outstanding characteristics:

(1) Its free and continuous production of blooms;

(2) The double petalage, but relatively small size of its blooms;

(3) The fragrance of its blooms; and (4) The distinctive yellow general color tonality of its blooms.

As compared with its seed parent, "Goldilocks," the bud form of the flowers of my new variety is urn-shaped, whereas that of "Goldilocks" is globular; the double petalage of the blooms of the new variety is attained by having an average petalage of from 30 to 35 petals, whereas the blooms of "Goldilocks" are more double and average approximately 45 petals; the petals of the open blooms of the new variety are substantially less reflexed than are the petals of the open blooms of "Goldilocks"; and the blooms of the new variety are smaller than those of the seed parent, measuring from 2 inches to 2½ inches, whereas those of "Goldilocks" measure from 3 inches to 3½ inches.

In comparison with its pollen parent "Pinocchio," the bloom color of my new variety is yellow, whereas that of "Pinocchio" is a light shade of pink, which is more popularly described as pink-suffused salmon; the blooms of the new variety have substantially more fragrance than do those of "Pinocchio"; and the plant of the new variety has a lower-growing habit than that of "Pinocchio," which latter variety is taller and more upright in its habit of growth.

The foregoing characteristics and distinctions definitely differentiate the new variety from its parents, as well as from all other varieties of its class of which I am aware, and asexual reproduction of the new variety by budding, as performed at Ontario, California, shows that its characteristics and distinctions come true to form and are established and transmitted through succeeding propagations.

The accompanying drawing shows typical specimens of the flowers, foliage and stems of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated:

Type: Bush; greenhouse and outdoors; seedling; for cut flowers and for garden decoration.

Class: Hybrid polyantha.

Breeding: Seedling.

*Seed parent.*—"Goldilocks."

*Pollen parent.*—"Pinocchio."

Propagation: Holds its distinguishing characteristics through succeeding propagations by budding.

FLOWER

Locality where grown and observed: Ontario, California.

Flowers borne: Several to stem; in regular, somewhat rounded clusters; on medium length stems of normal strength.

Quantity of bloom: From free to abundant, both outdoors and in greenhouse.

Continuity: Continuous during growing season.

Fragrance: Moderate. Nature—tea.

Bud:

*Peduncle.*—Average length; average caliper; erect; smooth; numerous gland-tipped cilia; few hairs. Color—between Kildare Green, Plate XXXI (Ridgway) and Absinthe Green, Plate XXXI (Ridgway), overlaid sometimes with near Indian Red, Plate XXVII (Ridgway) on side exposed to the sun.

*Before calyx breaks.*—Size—small. Form—medium length; ovoid; with foliaceous appendages and with some hairs on the surface of the bud; usually without much-cut foliaceous parts extending beyond the tip of the bud.

*As calyx breaks.*—Color—between Aureolin, Plate 3/1, page 3 (Wilson) and Lemon Yellow, Plate 4/2, page 4 (Wilson).

*Sepals (inner surface).*—With fine woolly tomentum; margins of alternate sepals lined with fine woolly tomentum; others lined with gland-tipped cilia.

*As first petal opens:*

Size—small.

Form—medium length; urn-shaped.

Color—outside—between Aureolin, Plate 3/1, page 3 (Wilson) and Lemon Yellow, Plate 4/2, page 4 (Wilson). Inside—Between Aureolin, Plate 3/1, page 3 (Wilson) and Lemon Yellow, Plate 4/1, page 4 (Wilson).

*Opening.*—Opens up well; is not retarded from opening by cold, hot, wet or dry weather.

Bloom:

*Size (when fully open).*—Small; from 2 inches to 2½ inches.

*Petalage.*—Double; from 30 to 35 petals, plus 8 to 12 petaloids; arranged regularly.

*Form.*—High-centered at first, becoming open later; petals at first being cupped, with lateral margins reflexed only slightly ⅓ or less of upper portion of petal, with lateral margins of outer petals sometimes reflexed ⅓ to ½ of upper portion of petal, and apex sometimes reflexed slightly, particularly on outer petals; becoming later at maturity flat-cupped, with lateral margins reflexed ½ or more of petal length, and with lateral margins of outer petals sometimes reflexed the entire length of the petal, and with apex sometimes reflexed, particularly on outer petals.

Petals:

*Texture.*—Thick; leathery; with inside satiny and outside shiny to satiny.

*Shape.*—Outside—broadly obovate, with apex flat; sometimes with 1 or 2 notches. Intermediate—obovate, with apex rounded to flat; sometimes with 1 or 2 notches. Inside—narrowly obovate; irregular; with apex rounded; sometimes with 1 or 2 notches.

This description of a newly opened flower was made from a rose grown outdoors in the month of August, at Ontario, California:

Color:

*Outside petal.*—Outside surface—between Aureolin, Plate 3/2, page 3 (Wilson) and Lemon Yellow, Plate 4/2, page 4 (Wilson). Inside surface—between Aureolin, Plate 3/1, page 3 (Wilson) and Lemon Yellow, Plate 4/2, page 4 (Wilson).

*Intermediate petal.*—Outside surface—between Aureolin, Plate 3/1, page 3 (Wilson) and Lemon Yellow, Plate 4/2, page 4 (Wilson). Inside surface—near Aureolin, Plate 3/1, page 3 (Wilson).

*Inner petal.*—Outside surface—near Aureolin, Plate 3/1, page 3 (Wilson). Inside surface—near Aureolin, Plate 3/1, page 3 Wilson).

This description was made from a rose that was open for 3 days outdoors in the month of August, at Ontario, California:

Color:

*Outside petal.*—Outside surface—between Canary Yellow, Plate 2/2, page 2 (Wilson) and Aureolin, Plate 3/3, page 3 (Wilson). Inside surface—between Canary Yellow, Plate 2/2, page 2 (Wilson) and Aureolin, Plate 3/1, page 3 (Wilson).

*Inside petal.*—Outside surface—between Canary Yellow, Plate 2/2, page 2 (Wilson) and Aureolin, Plate 3/2, page 3 (Wilson). Inside surface—between Canary Yellow, Plate 2/2, page 2 (Wilson) and Aureolin, Plate 3/1, page 3 (Wilson).

*General color effect.*—Newly opened flower—between Aureolin, Plate 3, page 3 (Wilson) and Lemon Yellow, Plate 4/1, page 4 (Wilson). 3-days open—between Canary Yellow, Plate 2/2, page 2 (Wilson) and Aureolin, Plate 3/2, page 3 (Wilson).

*Behavior.*—Drop off cleanly; not particularly affected by cold, hot, wet or dry weather.

*Flower longevity.*—On bush in garden—3 or 4 days in August. Cut roses grown outdoors and kept at living-room temperatures—4 days in August.

REPRODUCTIVE ORGANS

Stamens: Few; arranged irregularly about pistils; a few mixed with petaloids.

Filaments: From short to medium length; from 5 to 8 mm. in length; most with anthers.

*Color.*—Between Uranium Green, Plate 63/3, page 63 (Wilson) and Dresden Yellow, Plate 64/3, page 64 (Wilson).

Anthers: Medium size; all open approximately at once.

*Color.*—Upper side—margins near Saffron Yellow, Plate 7/1, page 7 (Wilson), with remainder near Primrose Yellow, Plate 601/3, page 65 (Wilson). Under side—Margins near Saffron Yellow, Plate 7/1, page 7 (Wilson), with remainder near Primrose Yellow, Plate 601/3, page 65 (Wilson).

Pollen: Moderate.

*Color.*—Between Indian Yellow, Plate 6/1, page 6 (Wilson) and Saffron Yellow, Plate 7/2, page 7 (Wilson).

Pistils: Few; approximately 35 in number.

Styles: Moderately even; average length; from thin to average caliper; somewhat loosely bunched; from 6 to 10 mm. in length.

*Color.*—Near Uranium Green, Plate 63/3, page 63 (Wilson).

Stigma:

*Color.*—Between Uranium Green, Plate 63/1, page 63 (Wilson) and Dresden Yellow, Plate 64/2, page 64 (Wilson).

Ovaries: Usually most enclosed in calyx, but some protruding from calyx.

Hips: Average length; globular; smooth; walls thick and fleshy.

*Color (1/2 mature).*—Near Lettuce Green, Plate V (Ridgway).

Sepals: Permanent; medium length; recurved.

*Color.*—Inside—between Biscay Green, Plate XVII (Ridgway) and Bice Green, Plate XVII (Ridgway), masked by White woolly tomentum. Outside—between Biscay Green, Plate XVII (Ridgway) and Bice Green, Plate XVII (Ridgway).

Seeds: Average number; medium size; from 5 to 8 in number.

PLANT

Foliage:

*Leaves.*—Compound of usually 5 to 7 leaflets; from normal to abundant quantity; medium size; somewhat leathery; semi-glossy.

*Leaflets.*—Shape—ovoid, with acute apex. Base—Round. Margin—simply serrate.

*Color.*—Mature—upper surface—between Forest Green, Plate XVII (Ridgway) and Dark Dull Yellow-Green, Plate XXXII (Ridgway); under surface—Near Light Elm Green, Plate XVII (Ridgway). Young—upper surface—near Bice Green, Plate XVII (Ridgway), bordered around margins with near Dark Corinthian Purple, Plate XXXVIII (Ridgway); under surface—near Light Elm Green, Plate XVII (Ridgway), bordered around margins with near Dark Corinthian Purple, Plate XXXVIII (Ridgway).

*Rachis (the supporting stem of the compound leaf).*—Average size. Upper side—grooved; hairy; with some stipitate glands on edges. Under side—with stipitate glands and 2 or 3 prickles.

*Stipules.*—Medium length; from medium width to wide; with medium length points turning out at an angle of more than 45°.

*Disease resistance.*—Better than average resistance to mildew as compared with other varieties grown under comparable cultural conditions at Ontario, California.

Growth:

*Habit.*—Bushy; upright-spreading; much-branched.

*Growth.*—Free.

*Canes.*—Medium caliper.

*Main stems.*—Color—between Light Elm Green, Plate XVII (Ridgway) and Bice Green, Plate XVII (Ridgway). Large prickles—few to several; from medium length to long; almost straight; with medium length, narrow base. Color—near Light Grayish Olive, Plate XLVI (Ridgway). Small prickles—very few. Color—near Light Grayish Olive, Plate XLVI (Ridgway). Hairs—none.

*Branches.*—Color—between Biscay Green, Plate XVII (Ridgway) and Light Elm Green, Plate XVII (Ridgway). Large prickles—from few to several; from medium length to long; almost straight; with medium length, narrow base. Color—between Fawn Color, Plate XL (Ridgway) and Wood Brown, Plate XL (Ridgway). Small prickles—very few. Color—near Wood Brown, Plate XL (Ridgway). Hairs—none.

*New shoots.*—Color—between Kildare Green, Plate XXXI (Ridgway) and Absinthe Green, Plate XXX (Ridgway), sometimes overlaid lightly with near Mineral Red, Plate XXVII (Ridgway).

Large prickles—from few to several; from medium length to long; almost straight; with medium length, narrow base. Color—near Courge Green, Plate XVII (Ridgway). Small prickles—few. Color—near Courge Green, Plate XVII (Ridgway). Hairs—none.

I claim:

A new and distinct variety of rose plant of the hybrid polyantha class, substantially as herein shown and described, characterized particularly as to novelty by its free and continuous production of blooms, the relatively small size and good fragrance of its blooms, the double petalage and distinctive yellow general color tonality of its blooms, and by its suitability for both greenhouse production of cut flowers and for garden decoration.

No references cited.